United States Patent [19]

Martin et al.

[11] 4,065,373
[45] Dec. 27, 1977

[54] HYDROGEN PATCH CELL

[75] Inventors: Richard L. Martin, Brentwood; Eddie C. French, Manchester, both of Mo.

[73] Assignee: Petrolite Corporation, St. Lous, Mo.

[21] Appl. No.: 680,024

[22] Filed: Apr. 26, 1976

[51] Int. Cl.² ............................................ G01N 27/46
[52] U.S. Cl. ........................... 204/195 C; 324/65 CR; 23/230 C
[58] Field of Search .................. 204/16, 195 C, 195 R, 204/195 P; 73/19, 23, 86; 324/29, 33, 65 CR, 71 R; 23/230 C

[56] References Cited

U.S. PATENT DOCUMENTS

| | | | |
|---|---|---|---|
| 2,886,497 | 5/1959 | Butler | 204/1 |
| 2,946,952 | 7/1960 | Marsh et al. | 324/71 R |
| 3,197,698 | 7/1965 | Schaschl et al. | 324/65 |
| 3,241,056 | 3/1966 | Lawrence, Jr. | 324/33 |
| 3,357,903 | 12/1961 | Lawrence, Jr. | 204/45 |
| 3,565,769 | 1/1971 | Holden et al. | 204/1 |
| 3,669,864 | 6/1972 | Fike | 204/195 R |

OTHER PUBLICATIONS

E. Gileadi, "Hydrogen Embrittlement Resulting from Corrosion, Cathodic Protection & Electroplating", Contract No N156-46659, Sept. 1966.

Primary Examiner—John H. Mack
Assistant Examiner—Aaron Weisstuch
Attorney, Agent, or Firm—Sidney B. Ring; Hyman F. Glass

[57] ABSTRACT

A hydrogen patch cell for measuring hydrogen atoms produced in the corrosion of ferrous metals. The cell mounts on the diffusion side of a ferrous wall being penetrated by hydrogen atoms and comprises a body having a cavity enclosed by an insulating impervious material. An electrolyte in the cavity provides an environment for the conversion of hydrogen atoms to ions. An end portion of the body carries a fluid-tight seal to the ferrous wall. An inert barrier within the body adjacent the end portion interposes between the cavity and the ferrous wall, adjacent to the wall. The barrier is permeable to hydrogen atoms but impermeable with respect to the electrolyte. A coupling material fills the void between the barrier and the ferrous wall and this material is inert but permeable to hydrogen atoms. Electrodes on the body connect to external circuitry for the electrochemical conversion of hydrogen atoms to ions which enter the electrolyte. One electrode in the electrolyte is a planar metal electrode coextensive with the barrier.

17 Claims, 5 Drawing Figures

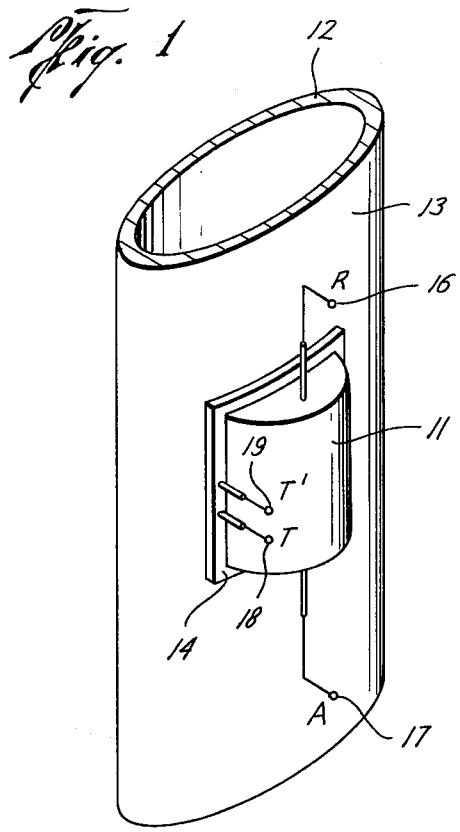
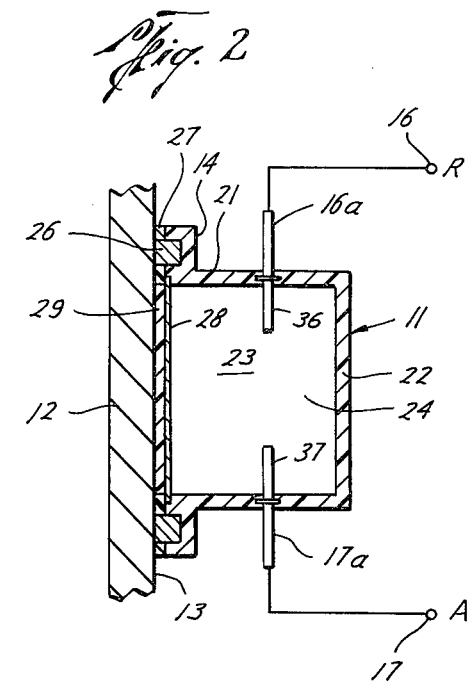
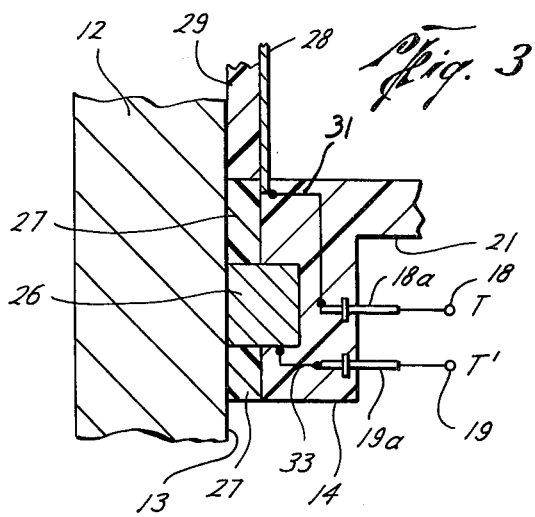
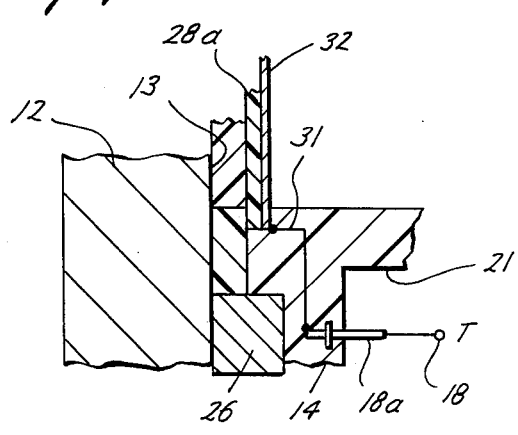
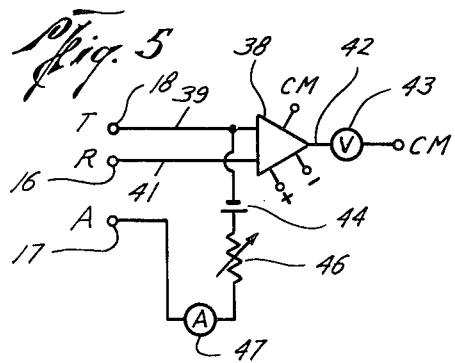

HYDROGEN PATCH CELL

BACKGROUND OF THE INVENTION

1. Field of the Invention

This invention relates to measuring and testing of corrosion processes, and it relates more particularly to an electrochemical cell system for measuring atomic hydrogen created by the corrosion of ferrous metals.

2. Description of the Prior Art

It is often desirable to determine the rates at which ferrous metals corrode within a corrodant, such as a corrosive aqueous liquid. For example, corrosion inhibitors are added to aqueous liquids to reduce the corrosion of exposed metals. Instruments are used to measure the rates at which these metals corrode so that the effectiveness of inhibitor addition can be determined. One measurement of the rate of corrosion upon ferrous metals involves the determination of the amount of atomic hydrogen created by the corrosion reaction of a ferrous metal exposed to a corrodant. For example, a steel sidewall of a pipeline carrying a corrodant, such as hydrogen sulfide in water, has a corrosion reaction creating atomic hydrogen which defuses through the sidewall and released exteriorly as molecular hydrogen gas. However, the molecular or atomic hydrogen inside the sidewall can oftentimes build up to a sufficient pressure causing physical injury such as blistering and rupturing of the sidewall metal.

Various measurement systems have been proposed for the measurement of the hydrogen produced by the corrosion reaction. For this purpose, a probe may be inserted through the sidewall of the pipeline and arranged to measure the molecular hydrogen gas pressure buildup within the probe. For this purpose, the probe has a ferrous metal body in which there is formed a cavity. The corrosion reaction produced by the corrodant surrounding the probe causes molecular hydrogen gas to accumulate within the cavity. A pressure guage mounted atop the probe indicates the actual pressure of hydrogen gas accumulating within the cavity. For example, in very active corrodants, the pressure buildup of such a probe can reflect hydrogen gas accumulations within the cavity from an initial 15 psi to about 100 psi or more within a 24-hour period. The probe carries a manual venting valve so that the pressure can be released from the cavity when the pressure limits of the guage are reached. Thus, this type of hydrogen measurement probe must be employed in a supervised manner wherein the operator can periodically record the readings of the probe and also vent hydrogen gas as necessary to prevent the destruction of the pressure guage. This type of hydrogen measurement probe is simple and relatively inexpensive but has not found extensive utilization in the industry because of the requirement for relatively constant supervision.

Another type of hydrogen measurement probe avoids the supervision problem but employs a sophisticated gas ionization instrumentation principle. In this probe, the hydrogen gas is vented in a relatively continuous manner from the cavity within the probe body. The vented gas flows through an ionization chamber and detector sensor whose output is measured upon a scalar instrument indicating both total gas volume and rate of gas flow. This probe and readout instrumentation is relatively accurate, very expensive and dependable, but requires careful calibration and complicated installation. Also, this probe is relatively too delicate to use unattended within oil fields, refineries and chemical plants.

Hydrogen gas amounts diffusing from a ferrous metal may be determined by an electrochemical method. In particular, this method measures the amount of hydrogen by electrochemical conversion of hydrogen gas to hydrogen ions. Potentiostatic or coulometric circuitry can provide the required current to affect the conversion from gas to ion forms of hydrogen and this current is directly proportional to the hydrogen permeation rate. An example of such a measurement is through the use of a "barnacle electrode" described in a publication, "Hydrogen Embrittlement Resulting from Corrosion, Cathodic Protection, and Electroplating," prepared by E. Gileadi and submitted by the Electrochemistry Laboratory of the University of Pennsylvania to the Naval Air Engineering Center, U.S. Navy in September 1966.

The "barnacle electrode" was developed for use with individual steel specimens and utilizes the electrochemical method for determination of the permeation rate of hydrogen. A small section is taken of the metal to be tested, and this metal specimen is cleaned and then placed into a glass electrolytic cell containing counter (auxiliary) and reference electrodes. The glass cell is filled on one side of the specimen with an electrolyte which may be an alkaline solution (0.2 N NaOH). The other side of the specimen is exposed to a source of hydrogen. If desired, a thin coating of palladium on the diffusion side of the test specimen may be employed to avoid anodic dissolution of the base metal by the electrolyte. The test specimen forms the test electrode of the system. The potential between the test and the reference electrodes is set at the required value so that substantially all of the hydrogen atoms are converted immediately to hydrogen ions upon entering into the electrolyte from the test specimen. The current flow required for this purpose is determined employing the counter electrode (which may be a silver silver oxide type). An integration of the current as a function of time produces the total amount of hydrogen diffusing through the specimen. Alternatively, the concentration of hydrogen diffusing from the specimen may be obtained from the shape of the current-time transient obtained from the cell. This technique requires a knowledge of the diffusion coefficient of hydrogen in the metal being tested. However, in any event, a small individual test specimen of the ferrous metal desired to be measured for hydrogen gas diffusion must be obtained and placed directly into the cell as an active element. As will be apparent, such an arrangement is impractical to be used in operating plants or in other than laboratory locations.

In many commercial installations, such as oil refineries and chemical plants, the integrity of the piping should not be disturbed for the placement of a hydrogen measuring probe system. This is especially true of the electric power generating plants employing atomic energy sources. In many of these plants, very pure water is employed for heat transfer or as a moderating fluid. In addition, the piping contains relatively high pressures and temperatures with a limited number of entry points which are constantly monitored so that any possible escape of radioactive material can be avoided. As is apparent, corrosion in such piping seriously contaminates the water being employed for the mentioned purposes. In particular, corrosion products entering the water would become radioactive. This undesired corrosion product would then become a source of atomic contamination throughout the electric power generating system. The number of entry points into the piping for introduction of corrosion measurement probes is extremely limited and of serious design nature. However, the corrositivity of the water contained in the piping must be measured to insure safe operation. It would be most desirable to employ a hydrogen measurement probe system with the water piping of a type not requiring special openings into the pipe, disrupting the integrity of the piping, or in any way jeopardizing the strength of the piping through induced external surface corrosion.

The hydrogen patch cell of the present invention provides a simplicity in construction and use in any environment without requiring a disruption of the integrity of piping or otherwise exposing the system to injury. In addition, this hydrogen patch cell produces the measurement of hydrogen diffusion in metallic walls with great utility and high accuracy equal to the best known prior art electrochemical methods.

SUMMARY OF THE INVENTION

In accordance with this invention, there is provided a hydrogen patch cell mountable on the diffusion side of the metallic wall being penetrated by hydrogen atoms. The cell has a body which carries an enclosure forming a cavity that contains an electrolyte for providing an electrochemical environment for the conversion of hydrogen atoms to hydrogen ions. An end portion of the body carries sealing means for providing a fluid-tight seal to the ferrous wall when the end portion is mounted in an operative position on the wall. A barrier is integrally carried in the body adjacent the end portion. This barrier is interposed between the cavity and the ferrous wall. The barrier is permeable to hydrogen atoms, but inert and impermeable with respect to the electrolyte contained in the cavity. A coupling material substantially fills all voids between the barrier and the adjacent ferrous wall. This coupling material is noncorrosive to the metallic wall, but it is permeable to hydrogen atoms. Electrode means are carried by the body for connection to an external circuitry whereby electrochemical conversion of hydrogen atoms to hydrogen ions is produced in the electrolyte. The electrode means include, in the electrolyte, a planar electrode coextensive with the barrier. In this manner, the entry into the electrolyte of any hydrogen atom immediately results in their conversion to hydrogen ions.

DESCRIPTION OF THE DRAWINGS

FIG. 1 is an elevation illustrating the hydrogen patch cell in operative placement upon a ferrous pipe carrying a corrosive fluid;

FIG. 2 is a vertical section taken through the hydrogen patch cell of FIG. 1;

FIG. 3 is a partial horizontal section, as an enlarged view, of the right side of the hydrogen patch cell shown in FIG. 1;

FIG. 4 is a partial horizontal section, as an enlarged view, of an alternate embodiment of the hydrogen patch cell shown in FIG. 1; and FIG. 5 is schematic of potential controlling circuitry for practicing an electrochemical method for determination of hydrogen diffusion employing the hydrogen patch cell of FIG. 1.

DESCRIPTION OF SPECIFIC EMBODIMENTS

FIG. 1 illustrates one embodiment of the hydrogen patch cell 11 of the present invention mounted in operable position upon the diffusion side of a ferrous wall being penetrated by hydrogen atoms, which wall may be a ferrous pipe 12 conveying a fluid contaminated with hydrogen sulfide or other hydrogen producing substance. The pipe 12 has an exterior surface 13 upon which the cell 11 is mounted. For purposes of description, corrosion occurring within the pipe 12 causes hydrogen gas to diffuse exteriorly from the surface 13 into the cell 11. The cell 11 is secured in fluid-tight engagement to the surface 13 so that all diffusing hydrogen gas in the cell covered area passes into the cell 11.

Preferably, the cell 11 is constructed with an end portion 14 that is adapted to conform to the surface 13. For example, the cell 11 is constructed of a polymeric resilient material (e.g., polyvinylchloride, synthetic rubber, etc.) so that the end portion 14 readily conforms to the configuration of the surface 13. The precise surface configuration can be formed into the end portion 14 during manufacture. However, the cell 11 can be constructed of a flexible material which permits ready hand-forming of the end portion 14 to the surface 13 at the time of installation.

The cell 11 for best results carries a plurality of electrode terminals 16, 17, 18 and 19, which provide functional connections to internally disposed reference (R), auxiliary (A), test (T) electrodes and an external test (T') electrode, respectively. The electrodes are employed with external circuitry for conducting the electrochemical method for determining hydrogen diffusion. If desired, only the reference and test electrodes may be used for potentiostatic or coulometric analysis techniques by those skilled in the art.

Referring to FIG. 2, the cell 11 is comprised of a body 21 carrying an enclosure 22 forming a cavity 23 containing an electrolyte 24 providing an electrochemical environment for the conversion of hydrogen atoms to hydrogen ions. The body and enclosure may be formed individually, or integrally, of any suitable materials. Preferably, the body 21 and the enclosure 22 are formed integrally of an insulating resilient material. Preferably, this material is sufficiently resilient so as not to be readily broken by physical impacts to the cell 11 in actual field use during hydrogen diffusion determinations. For example, the body 21 can be molded from a polypropylene thermosetting plastic. Alternatively, the body 21 may be formed of one material and only the enclosure 22 formed of the insulating material as long as the electrodes in the cavity 23 are maintained in electrical isolation from the pipe 12.

Preferably, the body 21 is highly flexible and integrally carries the end portion 14 conforming to the surface 13. The end portion 14 surrounds the periphery of the body 21 adjacent the surface 13 when the cell 11 is in operative position upon the pipe 12. The cell 11 can be held against the pipe 12 by bands or clamps. Also, the cell 11 at the end portion 14 can be held releaseably in operative position upon the surface 13 by a magnetic strip 26 imbedded within the end portion 14 and presented toward the surface 13. The strip 26 could be continuous, in segments, or even formed by individual magnets suitably spaced within the end portion 14. However, the cell 11 can be secured to the pipe 12 in high vibration areas, or for other reasons, by a contact adhesive 27 on the end portion 14 in addition to, or as a substitute for the magnetic strip 26. Preferably, the magnetic strip 26 secures the cell 11 against the pipe 12, and the contact adhesive 27 provides a peripheral fluid-tight seal between the end portion 14 and the surface 13. If desired, the peripheral seal may be provided by a material other than the contact adhesive 27. Advantageously, the contact adhesive 27 providing a holding and sealing function. In this arrangement, the cell 11 carries a removable protective covering of paper or thin metal prior to its installation upon the pipe 12. This covering material (not shown) allows the cell 11 to be safely handled without accumulating deleterious materials such as dirt prior to use.

The electrolyte 24 substantially fills the cavity 23 and is sealed within the body 21 by a barrier 28 integrally carried within the body 21. The barrier 28 can be molded with its peripheral edge embedded within the interior side surface of the material forming the body 21. Other arrangements for integrally securing the barrier 28 in the body 21 can be employed if desired. With such arrangements, the electrolyte 24 can be introduced through a filling port (not shown) or by hypodermic needle if desired. This filling opening is then sealed fluid-tight in the enclosure 22.

The barrier 28 should be of a material that is inert and impermeable with respect to the electrolyte 24. Importantly, the barrier should be permeable to hydrogen atoms so that the hydrogen diffusing from the surface 13 passes readily through the barrier 28 directly into the electrolyte 24. For example, the barrier 28 can be a thin (1 mm) noncorroding metal sheet. The barrier 28 is spaced a small distance from the surface 13, and in this intervening space, there is placed a coupling material which substantially fills the void. The coupling material is selected to be noncorrosive but highly permeable to hydrogen atoms. The coupling material 29 has two important functions. One function is to prevent the occlusion of air, or any deleterious fluid, from being entrapped in significant amounts between the surface 13 and the barrier 28. In the other function, the coupling material 29 protects the barrier 28 from inadvertent injury or puncture arising from physical handling or placement upon the pipe 12. Many suitable materials can be employed for the coupling material 29, for example, a pliant material such as a soft pliable wax. It is preferably to use a coupling material that is also sticky or tacky to provide adhesive results for the operative positioning of the cell 11 upon the pipe 12. The tacky waxes are especially useful for this purpose, and Eastabond 5T gives good mounting properties to the cell 11. With the tacky waxes for the coupling material, the cell 11 is easily installed upon the pipe 12, used for the desired period of time, and then removed by simply peeling the end portion 14 from the surface 13.

Referring now to FIG. 3, like elements have like designations in the cell 11 shown in FIGS. 1 and 2. Preferably, the barrier 28 is a thin sheet of palladium. However, other equivalent metals can be employed for this purpose. These metals may have the properties of occluding hydrogen in the atomic form, absorbing gaseous hydrogen in crevices extending to their external surfaces, the entrapment within the metal's lattic structure of hydrogen, and the ready permeation of hydrogen throughout their lattice structures. If the barrier 28 is an electrically conductive material, such as palladium, it can also serve as an electrode (test) in the electrochemical method for conversion of hydrogen atoms to hydrogen ions in the electrolyte 24. For this purpose, an electrical connection to the terminal 18 is made to the barrier 28 by a lead 31 within the body 21 and extending to a terminal pin 18a embedded within the body. The terminal pin 18a may have a flanged portion within the body 21 to firmly secure it in place.

It may be desired in the electrochemical method of determining hydrogen diffusion to compare the barrier 28 to the surface 13 as test specimen electrodes. For this purpose, a terminal pin 19a is embedded within the body 21 and connected by a lead 33 to terminal 19 and the magnetic strip 26 or other suitable metal-to-metal contact with the surface 13 of the pipe 12. Thus, the terminal 19 provides the connection to the alternate test electrode.

Referring to FIG. 4, an alternate embodiment of the cell 11 in construction of the barrier is shown and like elements have like numerals relative to the FIGS. 1–3 for convenience in description. In this embodiment, the barrier 28a is provided by an insulating material such as Teflon ® plastic, or other nonconductor, which is inert to the electrolyte but highly permeable to hydrogen. With this arrangement, a planar metal electrode 32 is mounted coextensively with the barrier 28a within the body 21. The metal electrode 32 can be a grid (perforate) of a suitable metal mounted adjacent the barrier 28a. Alternatively, the planar metal electrode 32 can be a thin film of hydrogen permeable metal plated or mounted directly upon the barrier 28a. Irrespective of the construction of the planar metal electrode 32, it is connected by the lead 31 to the terminal 18 as described in the previous embodiment.

Returning now to FIG. 2, additional electrodes may be provided the cell 11. For example, a reference electrode 36 and auxiliary electrode 37 may be insulated metal rods embedded in enclosure 22 and extending into the electrolyte 24 within the cavity 23. These electrodes connect to terminals 16 and 17. Portions of these rods form terminal pins 16a and 17a and may contain flanged parts within the body 21 to prevent inadvertent displacement. The rods 36 and 37 can be formed of steel, copper or other suitable metals for carrying out the electrochemical method for the conversion of hydrogen atoms to hydrogen ions within the electrolyte 24.

The electrolyte 24 can be an aqueous solution of sodium hydroxide, sulfuric acid or phosphoric acid or other like electrolytic material in which conversion of hydrogen atoms to hydrogen ions occurs at suitable potentials within the cell 11. The electrodes and the electrolyte 24 are selected so that the cell 11 in connection to external circuitry is capable of oxidizing quantitatively the hydrogen atoms which diffuse from the surface 13 through the barrier 28 into the electrolyte 24 into hydrogen ions. In the cell 11, the amount of hydrogen atoms entering the electrolyte 24 is proportional to the oxidation rate in conversion to hydrogen ions, and at quantum levels monitored by the electrodes.

More particularly, the electrodes in the cell 11 are useable to determine the hydrogen diffusing from the surface 13 by either potentiostatic or galvanic mode circuitry. For example, the test electrode 18 and the reference electrode 16 can be employed in a potentiostatic circuit. As a result, the oxidation of the hydrogen atoms to hydrogen ions in the electrolyte 24 is obtained by maintainence of a suitable potential difference between these electrodes. The resultant current flow between these electrodes through the electrolyte 24 is the measure of the hydrogen atoms being converted to hydrogen ions. If desired, a galvanic circuit produces an equivalent result using these electrodes.

However, it is preferred to use the cell 11 with three electrodes in a more effective electrochemical method for determination of hydrogen diffusion from the surface 13 into the electrolyte 24. For this purpose, a special circuit is employed for maintaining a certain potential difference between the test and reference electodes 28 and 36 by causing the precise current flow between the test and auxiliary electrodes 28 and 37 for maintaining such potential. The magnitude of current flow in this application is quantitative of the conversion of hydrogen atoms to hydrogen ions in the electrolyte 24. For this purpose, the circuitry shown in FIG. 5 can be employed. In this circuitry, a differential operational amplifier 38 has first and second inputs 39 and 41 connected, respectively, to the test and reference electrodes 28 and 36 in the cell 11. The output 42 of the amplifier 38 connects to circuit common of a suitable power supply (not shown) through a voltmeter 43 having a readout proportional to the potential difference between inputs 39 and 41. Current flow for the oxidation of the hydrogen atoms to hydrogen ions is provided by a battery 44 connecting through a rheostat 46 and ammeter 47 between the test and auxiliary electrodes 28 and 37, respectively. In operation of this circuit, the rheostat 46 is adjusted until the voltmeter 43 reads the desired level of polarization wherein the hydrogen atoms will be oxidized to hydrogen ions in the electrolyte 24. The current flow to produce this oxidization at the selected potential is determined from the current readout on the ammeter 47.

Other electrochemical methods may be employed with the cell 11, and likewise, instrumentation other than that shown in FIG. 5 could be employed. For example, the automated instrumentation shown in U.S. Pat. Nos. 3,717,566 and 3,924,175 can be used for good results. The diffusion rate is the instantaneous current readout, and the total hydrogen diffusion is provided by integration of these readouts over the period of interest.

In the selection of the electrolyte 24, some attention should be given to the temperature at which the cell 11 is to be used. For example, a 1% solution of sodium hydroxide as the electrolyte performs satisfactorily from room temperature up to about 60° C. However, at elevated temperature, background currents flowing through this electrolyte reduce the sensitivity of the cell 11 and may lead to excessive pressure buildups within the cavity 23. Preferably, an electrolyte of 85% phosphoric acid is used in the cell 11 since operating temperature can be in the range from ambient to about 150° C. and even higher without suffering undue loss of sensitivity in the electrochemical method of determining hydrogen diffusion. In many cases, the electrolyte can be concentrated sulfuric acid, and in particular, the concentration of the sulfuric acid is adjusted relative to operating temperature to optimize the sensitivity in use of the cell 11.

The potential to be maintained in the cell 11 between the test and reference electrodes in the electrochemical method for determining hydrogen diffusion will vary in magnitude from one type of electrolyte to another in the actual concentrations. However, selection of a particular electrolyte and concentration permits ready calibration of the cell 11 relative to the instrumentation used with it for the electrochemical method. Actual testing of the cell 11 shows capability for determining both actual (static) and also increasing and decreasing hydrogen diffusion rates and magnitudes through the surface 13 in periods of time 20 to 30 hours faster than can be obtained by conventional pressure buildup probes. In addition, at very low hydrogen diffusion rates, the response of a conventional pressure probe can be as low as 0.2 psi per hour where the pressure gauge readout is 0-60 psi in scale. Under the same hydrogen diffusion rate, the cell 11 can produce a readout of 40 to 50 microamps on the ammeter 47 having a full scale readout of 100 microamps. Thus, the cell 11 has a readability accuracy and sensitivity at least 150 times that of the pressure buildup probe. In additional, the cell 11 is capable of giving quantitative information as to diffusion rate and also the total magnitude of hydrogen diffusing from the surface 13 wherein the circuitry of the mentioned patents is employed.

The most important features of the present cell 11 are that it is readily applied to, used and removed from the exterior surface of any type of ferrous wall. No special preparation of such wall is required and the use of the cell 11 does not cause any injury to, contamination of, or leave a wall surface susceptible to subsequent corrosion problems.

Various modifications and alterations in the described hydrogen patch will be apparent to those skilled in the art from the foregoing description which do not depart from the spirit of the invention. For this reason, these changes are desired to be included within the scope of the appended claims. The appended claims define the present invention; the foregoing description is to be employed for setting forth the present embodiment as illustrative and not limited in nature.

What is claimed is:

1. A hydrogen patch cell mountable on the diffusion side of a metallic wall being penetrated by hydrogen atoms, comprising:
   a. a body formed of an insulating material, said body defining a cavity and having an open end portion adapted to conform to the surface configuration of a metallic wall, said cavity containing an electrolyte, said electrolyte providing an electrochemical environment for conversion of hydrogen atoms to hydrogen ions and said body being impervious to said electrolyte;
   b. securing means associated with said body for holding said end portion in engagement with the metallic wall;
   c. sealing means on said body for providing a peripheral fluid-tight seal between said end portion and said metallic wall;
   d. a noncorroding metal barrier adjacent said open end portion, said barrier being interposable between said cavity and said wall and separated from said wall only by pliant coupling material which substantially fills all voids between said barrier and said wall, said barrier being permeable to hydrogen atoms but inert and impermeable with respect to said electrolyte contained in said cavity; and
   e. electrode means carried internally by said body and extending externally for connection to external circuitry whereby electrochemical conversion of hydrogen atoms to hydrogen ions is produced in said electrolyte and hydrogen diffusion is determined.

2. The hydrogen patch cell of claim 1 wherein said metal barrier is a thin sheet of palladium.

3. The hydrogen patch cell of claim 1 wherein said electrolyte is an aqueous solution containing sodium hydroxide, sulfuric acid or phosphoric acid.

4. The hydrogen patch cell of claim 1 wherein said electrode means include said metal barrier providing a test electrode, and reference and auxiliary metal electrodes carried by said body immersed within said electrolyte.

5. The hydrogen patch cell of claim 1 wherein said body is formed of an insulating and resilient material having pliable characteristics permitting ready forming of said end portion into substantial conformity with the surface configuration of the metallic wall.

6. The hydrogen patch cell of claim 1 wherein said securing means are magnetic strip members integrally carried by said body for magnetic attraction engagement with the metallic wall.

7. The hydrogen patch cell of claim 1 wherein said sealing means is a surface contact adhesive.

8. A hydrogen patch cell mountable on the diffusion side of a metallic wall being penetrated by hydrogen atoms, comprising:
   a. a body carrying an enclosure of insulating, impervious material forming a cavity, said cavity containing an electrolyte providing an electrochemical environment for conversion of hydrogen atoms to hydrogen ions;
   b. sealing means carried by an open end portion of said body for providing a fluid-tight seal to a metallic wall when said end portion is mounted in operative position on said metallic wall;
   c. a barrier carried in said body adjacent said open end portion, said barrier interposable between said cavity and the metallic wall and adjacent to said wall, said barrier being permeable to hydrogen atoms but inert and impermeable with respect to said electrolyte contained in said cavity;
   d. coupling material adapted to substantially fill all voids between said barrier and the metallic wall adjacent thereto, and said coupling material being noncorrosive to the metallic wall and permeable to hydrogen atoms; and
   e. electrode means internally carried by said body and extending externally for connection to external circuitry whereby electrochemical conversion of hydrogen atoms to hydrogen ions is produced in said electrolyte and hydrogen diffusion is determined, said electrode means including in said electrolyte a planar electrode coextensive with said barrier.

9. A hydrogen patch cell mountable on the diffusion side of a metallic wall being penetrated by hydrogen atoms, comprising:
   a. a body carrying an enclosure of insulating, impervious material forming a cavity, said cavity containing an electrolyte providing an electrochemical environment for conversion of hydrogen atoms to hydrogen ions, an open end portion on said body being adapted to conform to the surface configuration of a metallic wall;
   b. securing means associated with said body for holding said end portion in engagement with said metallic wall;
   c. sealing means on said body for providing a peripheral fluid-tight seal between said end portion and said metallic wall;
   d. a barrier integrally carried in said body adjacent said open end portion, said barrier being interposable between said cavity and said metallic wall and adjacent to said wall, said barrier being electrically conductive and permeable to hydrogen atoms but inert and impermeable with respect to said electrolyte;
   e. electrode means internally carried by said body and extending externally for connection to external circuitry whereby electrochemical conversion of hydrogen gas to hydrogen ions is produced in said electrolyte and hydrogen diffusion is determined; and
   f. means electrically insulating said electrode means from the metallic wall, said cell when mounted on a metallic wall, being separated therefrom only by pliant coupling material.

10. A hydrogen patch cell moutable on the diffusion side of a metallic wall being penetrated by hydrogen atoms, comprising:
    a. a body carrying an enclosure of insulating impervious material forming a cavity, said cavity containing an electrolyte, said electrolyte providing an electrochemical environment for conversion of hydrogen atoms to hydrogen ions;
    b. sealing means carried by an open end portion on said body for providing a fluid-tight seal between a metallic wall and said open end portion when said end portion is mounted in operative position on a metallic wall;
    c. a barrier integrally carried in said body adjacent said end portion and interposable between said cavity and the metallic wall, adjacent to said wall, said barrier being permeable to hydrogen atoms but inert and impermeable with respect to said electrolyte contained in said cavity; and
    d. electrode means internally carried by said body and extending externally for connection to external circuitry whereby electrochemical conversion of hydrogen atoms to hydrogen ions is produced in said electrolyte and hydrogen diffusion is determined, said electrode means including in said electrolyte a planar metal electrode coextensive with said barrier,
    said cell when mounted on a metallic wall, being separated therefrom only by pliant coupling material.

11. The hydrogen patch cell of claim 10 where said planar metal electrode is a thin film of palladium plated or mounted directly on said barrier.

12. The hydrogen patch cell of claim 10 wherein said electrolyte is an aqueous solution containing sodium hydroxide, sulfuric acid or phosphoric acid.

13. The hydrogen patch cell of claim 10 wherein said electrode means includes said planar metal electrode providing a test electrode, and reference and auxiliary metal electrodes carried by said body and immersed within said electrolyte.

14. The hydrogen patch cell of claim 10 also comprising securing means associated with said body for holding said open end portion in engagement with the metallic wall.

15. A hydrogen patch cell mountable on the diffusion side of a metallic wall being penetrated by hydrogen atoms, comprising:
    a. a body formed of an insulating material, said body defining a cavity, and having its open end portion adapted to conform to the surface configuration of a metallic wall, said cavity containing an electrolyte, said electrolyte providing an electrochemical environment for conversion of hydrogen atoms to hydrogen ions and said body being impervious to said electrolyte;

b. sealing means on said body for providing a peripheral fluid-tight seal between said end portion and said metallic wall;

c. a barrier adjacent said open end portion, said barrier being interposable between said cavity and said wall and adjacent thereto and separated from said wall only by pliant coupling material which substantially fills all voids between said barrier and said wall, said barrier being permeable to hydrogen atoms but inert and impermeable with respect to said electrolyte contained in said cavity; and d. electrode means carried internally by said body and extending externally for connection to external circuitry whereby electrochemical conversion of hydrogen atoms to hydrogen ions is produced in said electrolyte and hydrogen diffusion is determined, said electrode means including in said electrolyte a planar non-corroding metal electrode coextensive with said barrier.

16. The hydrogen patch cell of claim 15 wherein said electrolyte is an aqueous solution containing sodium hydroxide, sulfuric acid or phosphoric acid.

17. The hydrogen patch cell of claim 15 also comprising securing means associated with said body for holding said open end portion in engagement with the metallic wall.

* * * * *